United States Patent
Cado

(10) Patent No.: US 10,809,248 B2
(45) Date of Patent: Oct. 20, 2020

(54) SYSTEM FOR CERTIFYING A DETECTION OF A GASEOUS SUBSTANCE EXHALED BY AN INDIVIDUAL, AND METHOD USING THE SYSTEM

(71) Applicant: APERLI, Paris (FR)

(72) Inventor: Jean-Jacques Cado, Paris (FR)

(73) Assignee: APERLI, Paris (FR)

( * ) Notice: Subject to any disclaimer, the term of this patent is extended or adjusted under 35 U.S.C. 154(b) by 254 days.

(21) Appl. No.: 15/767,890

(22) PCT Filed: Oct. 11, 2016

(86) PCT No.: PCT/EP2016/074268
§ 371 (c)(1),
(2) Date: Apr. 12, 2018

(87) PCT Pub. No.: WO2017/064023
PCT Pub. Date: Apr. 20, 2017

(65) Prior Publication Data
US 2018/0306776 A1      Oct. 25, 2018

(30) Foreign Application Priority Data

Oct. 12, 2015   (FR) ...................................... 15 59679
Jun. 23, 2016   (FR) ...................................... 16 55853

(51) Int. Cl.
*G01N 33/497*       (2006.01)
*B60K 28/06*       (2006.01)
(Continued)

(52) U.S. Cl.
CPC ........ *G01N 33/4972* (2013.01); *A61B 5/4845* (2013.01); *B60K 28/063* (2013.01); *G06K 19/06009* (2013.01)

(58) Field of Classification Search
CPC .............. G01N 33/4972; A61B 5/4845; G06K 19/06009; B60K 28/063
See application file for complete search history.

(56) References Cited

U.S. PATENT DOCUMENTS 6,956,848 B1    10/2005  Keung et al.
7,934,577 B2     5/2011  Walter et al.
(Continued)

FOREIGN PATENT DOCUMENTS

EP    2075151 A1     7/2009
EP    2127599 A1    12/2009
EP    2237034 A1    10/2010

OTHER PUBLICATIONS

International Search Report and Written Opinion dated Dec. 7, 2016 for corresponding International Application No. PCT/EP2016/074268, filed Oct. 11, 2016.
(Continued)

*Primary Examiner* — Eric S. McCall
*Assistant Examiner* — Timothy P Graves
(74) *Attorney, Agent, or Firm* — David D. Brush; Westman, Champlin & Koehler, P.A.

(57) ABSTRACT

A system for certifying a detection of a gaseous substance present in air exhaled by an individual. The system includes a sensor providing a measurement of the quantity of the gaseous substance, a portable terminal connected to the sensor and having a camera for taking an image of the individual. The terminal has a module for authenticating the individual and the sensor used for the exhaled air sample by analyzing the data of images using facial recognition and by analyzing a graphic marker for the sensor. The terminal produces an item of data representative of the quantity of gaseous substance measured in the sample and a piece of authenticated identification data of the individual who has exhaled the sample. The system can at the same time authenticate the identity of the individual, authenticate the sensor used, and associate the result of the value of the test with the individual.

17 Claims, 4 Drawing Sheets

Figure 3:
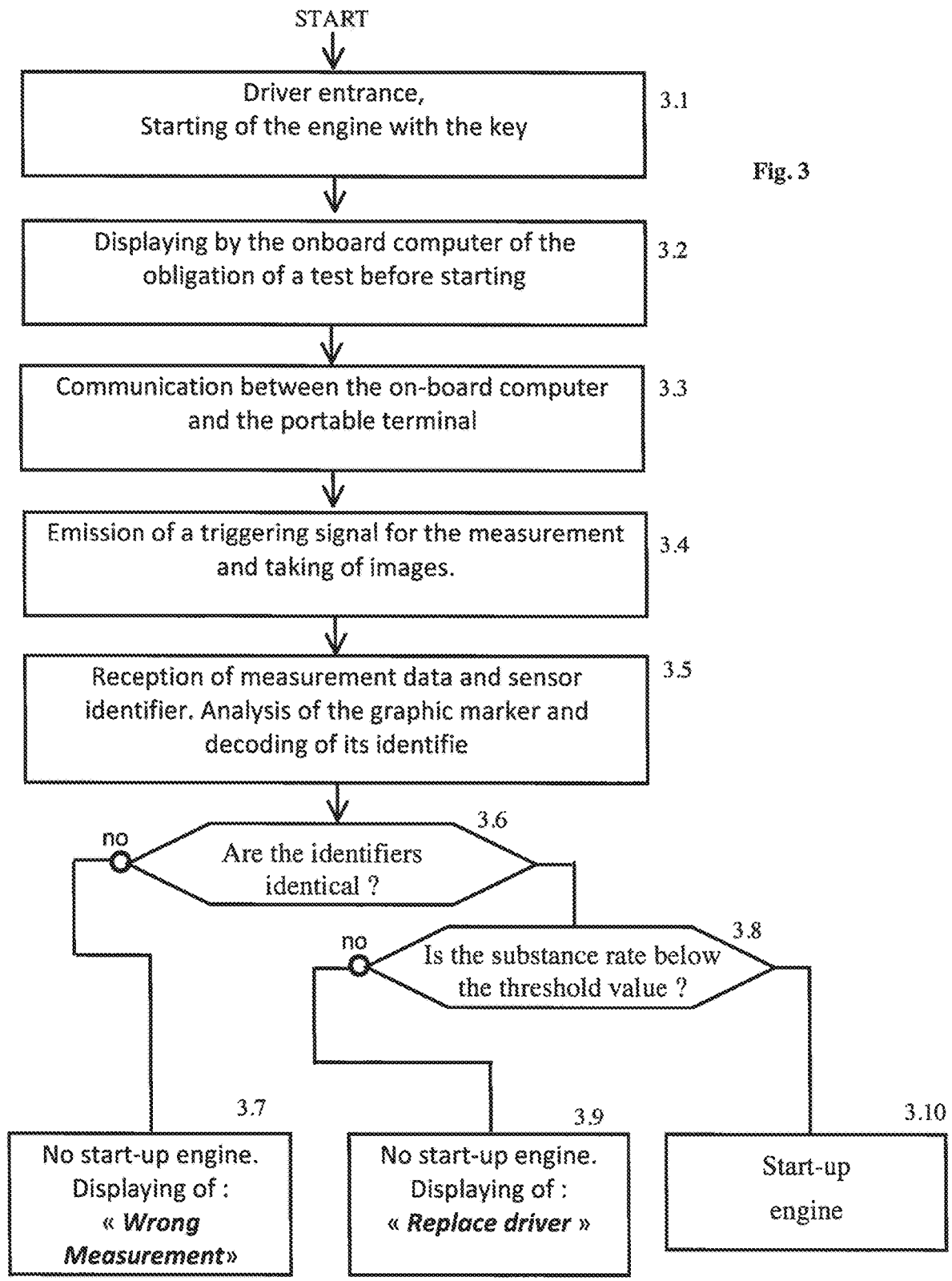

(51) Int. Cl.
*G06K 19/06* (2006.01)
*A61B 5/00* (2006.01)

(56) References Cited

U.S. PATENT DOCUMENTS

| | | | |
|---|---|---|---|
| 2009/0169068 A1* | 7/2009 | Okamoto | B60K 28/063 |
| | | | 382/118 |
| 2009/0293589 A1* | 12/2009 | Freund | G07C 5/0891 |
| | | | 73/23.3 |
| 2010/0012417 A1* | 1/2010 | Walter | B60K 28/063 |
| | | | 180/272 |
| 2010/0251804 A1 | 10/2010 | Morley et al. | |
| 2013/0021153 A1 | 1/2013 | Keays | |
| 2015/0204844 A1* | 7/2015 | Nothacker | G06K 9/00288 |
| | | | 73/23.3 |
| 2015/0212063 A1* | 7/2015 | Wojcik | G01N 33/4972 |
| | | | 340/576 |
| 2016/0341716 A1* | 11/2016 | Rodriguez | G01N 33/497 |

OTHER PUBLICATIONS

English translation of Written Opinion of the International Searching Authority dated Dec. 7, 2016 for corresponding International Application No. PCT/EP2016/074268, filed Oct. 11, 2016.

\* cited by examiner

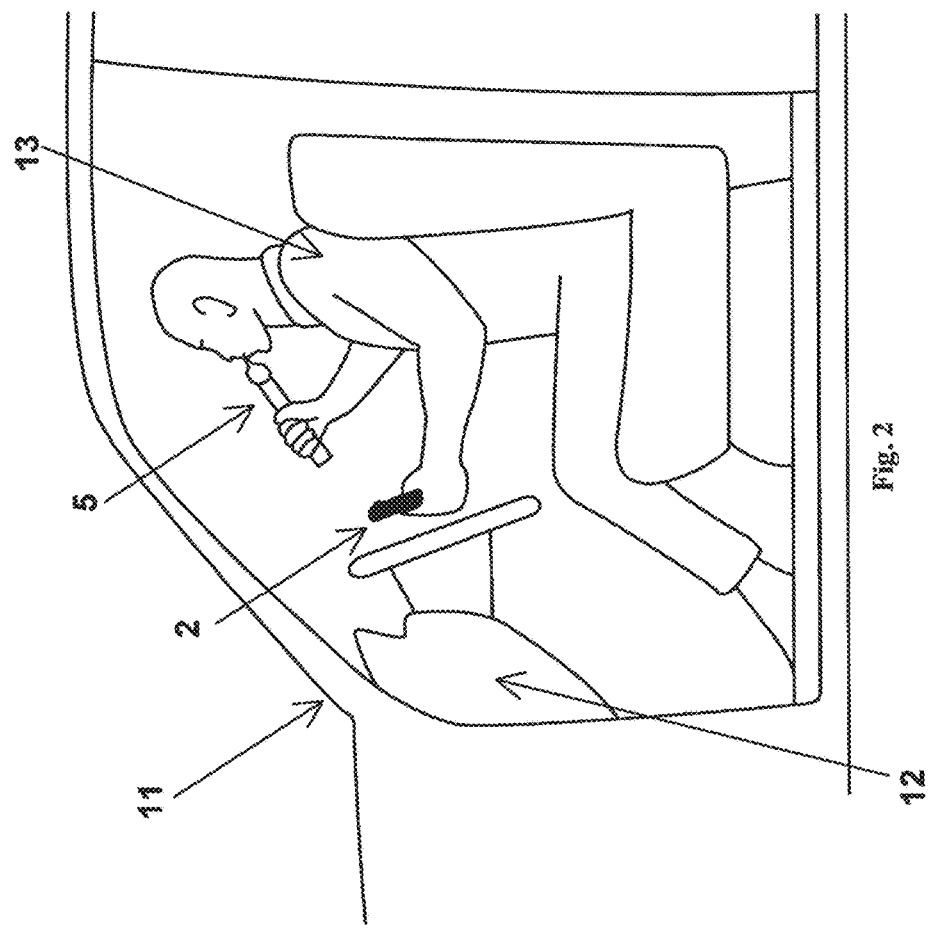
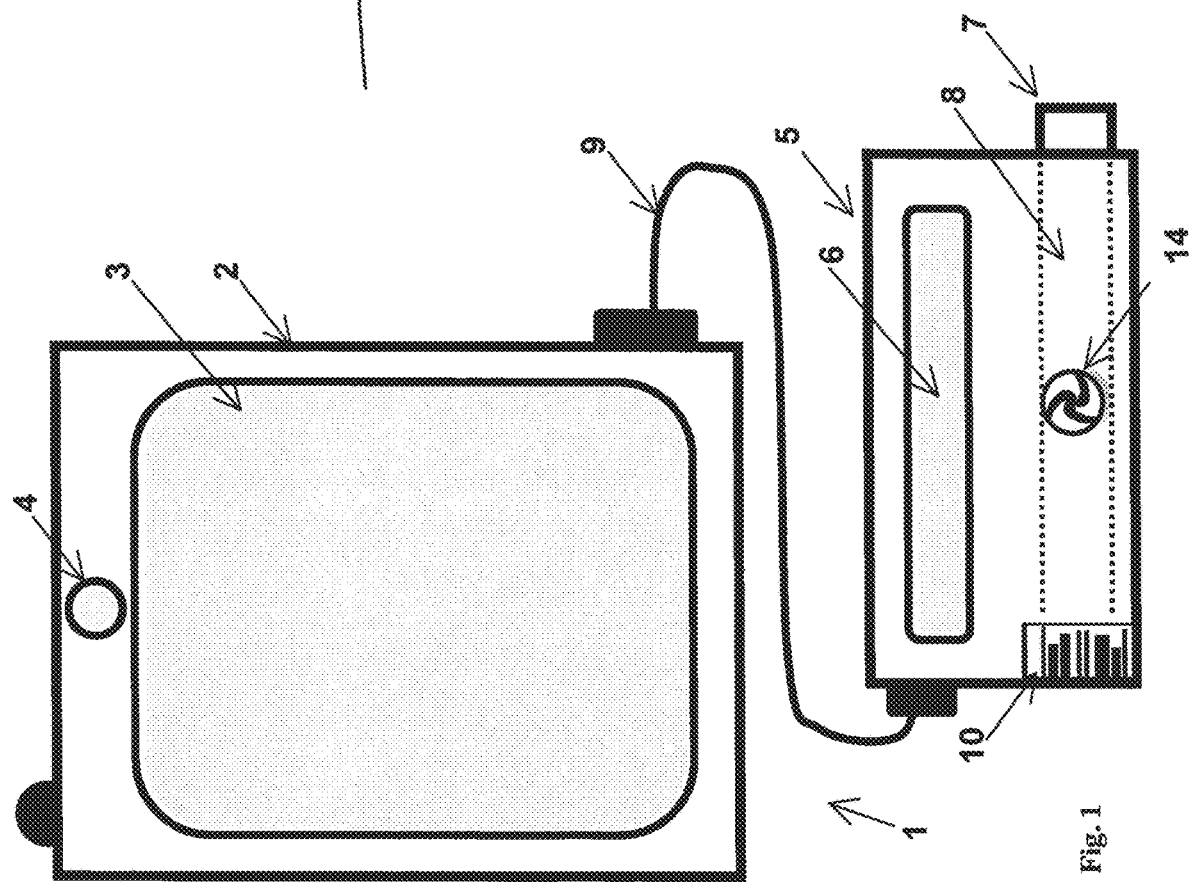

SYSTEM FOR CERTIFYING A DETECTION OF A GASEOUS SUBSTANCE EXHALED BY AN INDIVIDUAL, AND METHOD USING THE SYSTEM

CROSS-REFERENCE TO RELATED APPLICATIONS

This Application is a Section 371 National Stage Application of International Application No. PCT/EP2016/074268, filed Oct. 11, 2016, which is incorporated by reference in its entirety and published as WO 2017/064023 A1 on Apr. 20, 2017, not in English.

1. FIELD OF THE INVENTION

The invention concerns a system for certifying a detection of a gaseous substance present in the air exhaled by an individual, the system comprising a sensor connected to a portable terminal. The invention in particular concerns the fact that the camera of the terminal takes an image of the individual carrying out the test in order to authenticate said individual by facial recognition.

2. PRIOR ART

Alcoholism is currently becoming a real problem for society. In France, 45,000 deaths are related to excessive alcohol consumption each year. This corresponds to the second highest cause of preventable death in this country. Drugs such as cannabis and heroin also cause numerous deaths as a result of excess consumption. The damage caused by these substances sometimes go unnoticed, and the effects only appear gradually in time, by which point it is often too late. So-called "psychotropic" substances act on the central nervous system, altering some of the brain's biochemical and physiological processes. The brain functions are altered by changing the perception, sensations, mood, and as a whole the consciousness and behaviour of the consumer, which is why they are harmful.

Society condemns the use of such psychotropic substances, in particular when they are taken before driving. One of the main causes of death while driving is alcoholism. In addition to the sanctions imposed for driving with a blood alcohol level greater than the legislation in force, the effects of drinking and driving are known: narrowed visual field, reduced attention and resistance to drowsiness, slower reflexes, altered ability to assess distances, increased sensitivity to glare and excess self-confidence. In order to detect the absorption of such substances, the authorities are equipped with means for detecting the blood alcohol level or absorption of certain drugs. However, the frequency of checks is low and gives such measures little deterring power.

Drinking and driving can also be fought by developing the practice of self-testing. With this in mind, the authorities have recently brought in rules requiring owners to have at least one breathalyser in their vehicle. The purpose of a breathalyser is to show the alcohol content in the alveolar air exhaled in the breath of its user. It should be noted that this level is directly correlated to the blood alcohol level. Electronic breathalyser models recently marketed can be connected to a smartphone and measure the level of psychotropic substances exhaled by an individual. The measurement is emitted to the smartphone to be displayed. The smartphone user can therefore perform a self-test and decide, with full knowledge of the facts, whether or not to drive.

Nonetheless, if the individual does not carry out the test, or if the test is carried out but the individual's judgement is too altered, the individual may decide to drive and place himself/herself in danger. If the state of health of an individual is incompatible with driving a car, he/she must be prevented therefrom by any means. This attitude must be taken, regardless of the activity of said individual, and not only for driving a car. This test can also be carried out by pilots before take-off. The test can also be used as an incentive to encourage individuals to combat an addiction. The breathalyser can be used by a patient for therapeutic purposes for daily monitoring of the blood alcohol level and thus encourage a user to stop drinking.

U.S. Pat. No. 7,934,577 discloses a testing mechanism installed in a vehicle, requiring the driver to carry out a self-test using a breathalyser before taking the wheel. If the test result is positive (psychotropic substances have been detected and in proportions beyond a threshold) or if the test was not carried out, a control device prevents engine start-up. If the result is negative, the control device authorises the start-up of the engine. This document stipulates that the vehicle comprises one or more cameras allowing the driver to be identified. The cameras and the breathalyser are connected to the vehicle control device. However, this provision has the drawback of presenting an opportunity to cheat by making the driver blow into an unconnected breathalyser and another individual into the breathalyser actually connected to the vehicle control device. There is therefore a real need for a system certifying the authenticity of a test for detecting a gaseous substance applied to an identified individual.

Document U.S. Pat. No. 6,956,848 discloses a system for checking the identity of an individual consisting of the comparison of the image captured during the test with a previously captured image. This only works in the case of an ignition interlock breathalyser, when the limits of said device are known. Moreover, it is extremely difficult to provide an image-capture system in the case of an ignition interlock breathalyser.

3. PURPOSES OF THE INVENTION

This invention provides a solution that does not suffer from the drawbacks of the prior art. The solution proposed ensures that the measurement of the level of psychotropic substances is associated with an individual whose identity is recognised. This invention in particular prevents said individual from performing an activity that presents a risk to himself/herself or to people nearby.

4. DESCRIPTION OF THE INVENTION

This invention proposes a system for certifying a detection of a gaseous substance present in the air exhaled by an individual, said system comprising a sensor detecting said gaseous substance in the exhaled air. Said sensor comprises a unit for collecting and analysing a sample of air exhaled by said individual, capable of providing a measurement of the quantity of gaseous substance per unit of volume. Said system further comprises a portable terminal equipped with a means for communicating with the sensor so as to at least receive the measurement. The portable terminal is equipped with a camera intended to capture an image of the individual blowing into said sensor to perform a detection, and a module for authenticating the individual and the sensor used for said exhaled air sample by analysing the data of images using facial recognition for the individual and by analysing a graphic marker placed on the sensor. The terminal produces a set of information comprising an item of data representative of the quantity of gaseous substance measured in the sample and a piece of authenticated identification data of the individual who has exhaled said sample.

In this way, the system can at the same time authenticate the identity of the person who carries out the test, authenticate the sensor used for the test, and associate the result of the value of the detection with said person. This data can be used by any control system for authorising the person having carried out the test to perform a certain activity or prevent him/her therefrom if said person could endanger himself/herself or a group of individuals.

According to a first embodiment, the system comprises a control device in communication with the terminal, said device controlling the operation of a vehicle and authorising start-up thereof if the individual identified by the data received is authorised to drive said vehicle and if the measurement transmitted shows that the gaseous substance is not present or is present below a certain threshold. In this way, the vehicle can only be started if the detection result is negative.

According to another embodiment, the system comprises a means for emitting a sound integrated into a vehicle, such as a horn, the emitting means being activated when the measurement transmitted shows that the gaseous substance is present beyond a certain threshold. In this way, an audible signal is emitted warning the individual and persons nearby that the detection result is positive.

According to another embodiment, the system comprises a remote device communicating by radio with the portable terminal, the remote device emitting a signal to the portable terminal, said signal triggering the appearance of a menu displayed on a screen of the portable terminal and requesting the completion of a test, the portable terminal transmitting an information item to said remote device via the mobile phone network, said information item being representative of the measurement and the authenticated identification data of the individual. In this way, a device centralising data is constantly kept up-to-date of the status of the tests carried out on the members of an organisation.

According to another embodiment, the remote device triggers an alarm if no test producing a negative result has been correctly carried out during a given period of time. In this way, it is easier to identify an individual who has not been tested for a certain amount of time.

According to another embodiment, the portable terminal has a position determination means allowing the remote device to obtain the position thereof, the remote device transmitting the signal to the portable terminal, said signal triggering the appearance of a menu after immobilisation of the terminal for a minimum period of time. In this way, if a driver stops for food for example, the system detects this and asks the driver to carry out a test.

According to another embodiment, the portable terminal detects the activation by the individual of a device for the use thereof, the activation triggering the appearance of the menu requesting said individual to carry out a test. In this way, a test can be requested every time a user of a machine turns on said machine.

According to another embodiment, said sensor comprises an anemometer detecting the airflow resulting from an exhalation, the detection of an airflow resulting from an exhalation triggering the capture of at least one image. In this way, the image capture is synchronised with the exhalation of the individual, which limits cheating.

According to another embodiment, the graphic marker of the sensor is a visible indicator light on the side opposite that of a mouthpiece into which the individual blows when carrying out a test, the light beam emitted by said indicator having features that identify said sensor. In this way, it is easier for the terminal to authenticate the sensor.

According to another embodiment, at least one feature of the light beam emitted by the visible indicator light on the side opposite that of a mouthpiece is provided by the portable terminal via the communication means 9. In this way, the authentication of the sensor by the terminal is enhanced, which makes cheating by using another sensor practically impossible.

According to another embodiment, the graphic marker is a QR Code or a barcode placed on the side opposite that of a mouthpiece. In this way, it is easier for the terminal to authenticate the sensor and said authentication requires less computing power.

According to another embodiment, the terminal initialises communication with the sensor in order to ensure that a single sensor is connected. In this way, fraud by using at least two sensors is almost impossible.

According to another aspect, the invention relates to a method for certifying a detection of a gaseous substance present in the air exhaled by an individual by using a sensor detecting said gaseous substance in the exhaled air. This method comprises the steps of:

exhaling by said individual into the sensor in order to provide a measurement of the quantity of gaseous substance per unit of volume, capturing an image of at least the individual blowing into said sensor in order to carry out a test using the camera (4) of a portable terminal (2) connected to said sensor (5), authenticating the individual and the sensor used for said exhaled air sample by analysing the data of images using facial recognition for the individual and by analysing a graphic marker placed on the sensor, producing, by the terminal (2), a set of information comprising an item of data representative of the quantity of gaseous substance measured in the sample and a piece of authenticated identification data of the individual who has exhaled said sample.

According to another aspect, the invention relates to a computer program product available for download from a communication network and/or stored on a computer-readable medium and/or run by a central processing unit. Said computer program comprises program instructions for implementing at least one step of the method for certifying a detection of a gaseous substance as disclosed hereinabove and according to any of the embodiments.

5. LIST OF FIGURES

Figure 4:
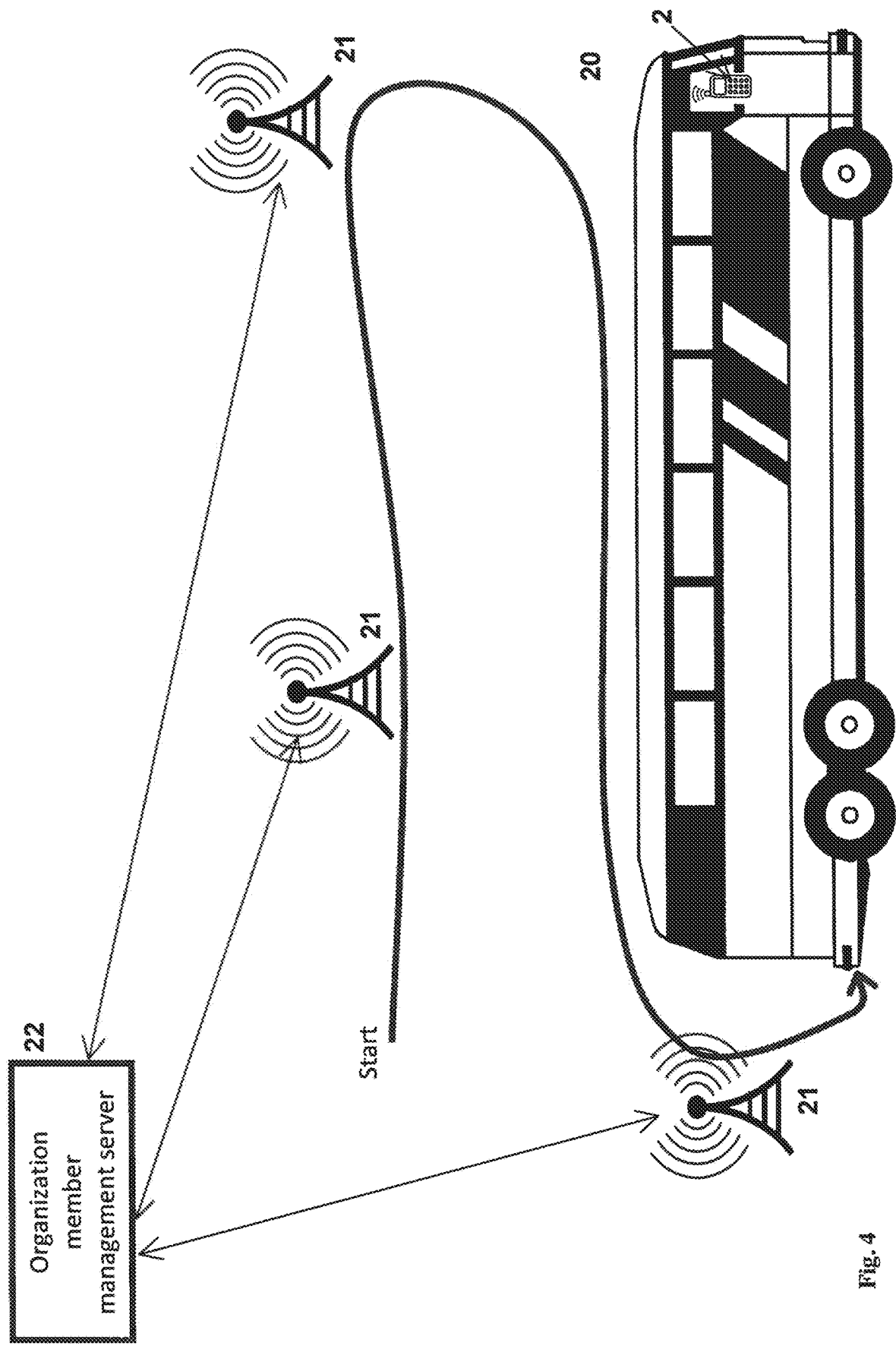
Figure 6:
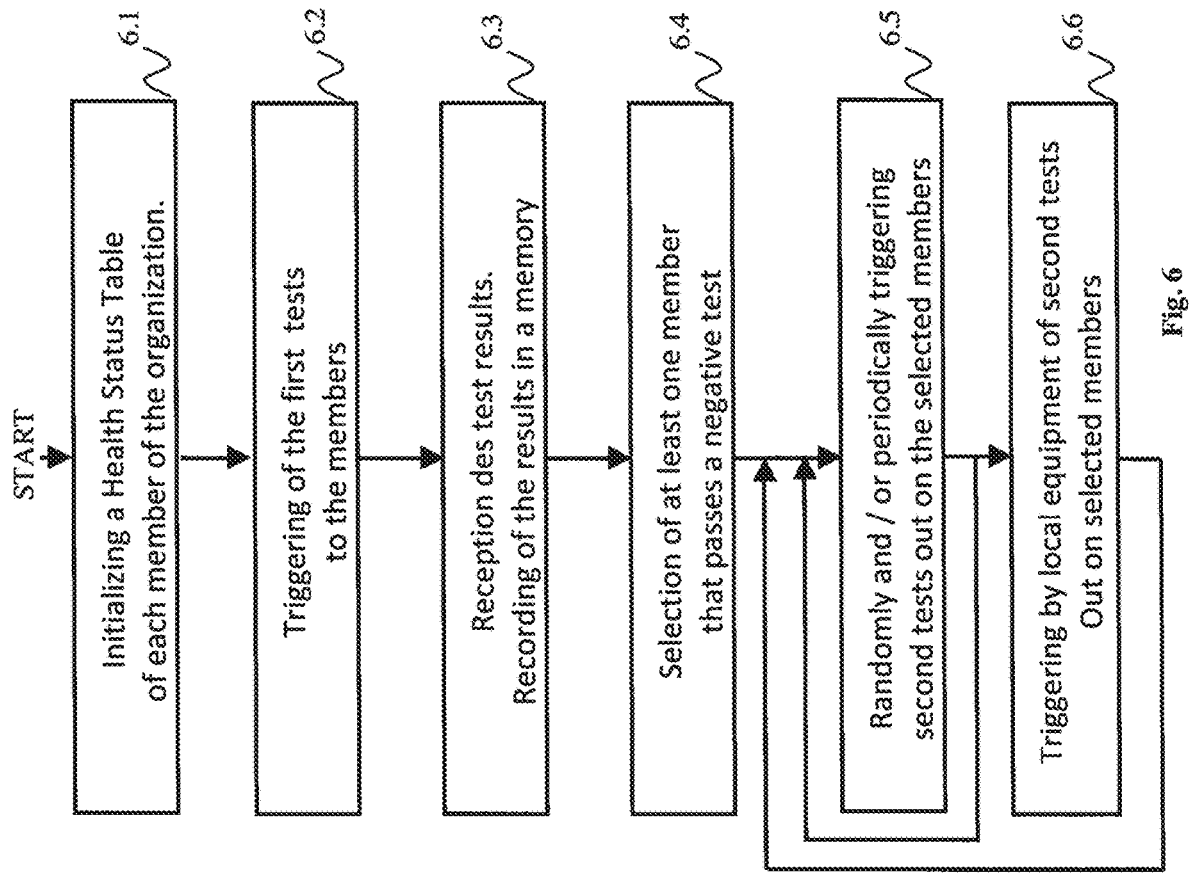
Figure 5:
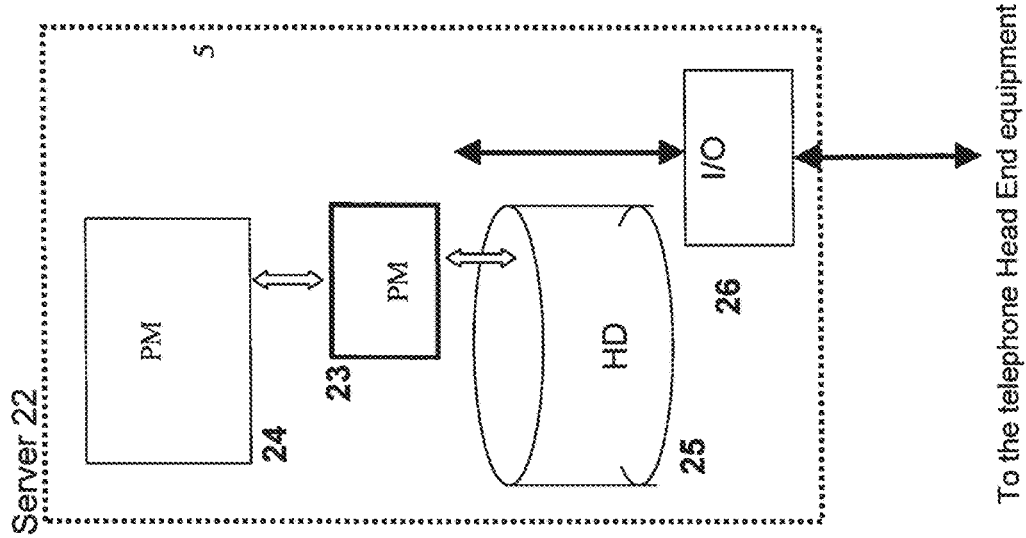

Other characteristics and advantages of the invention shall be better understood upon reading the following description given of a non-limitative example of embodiment of the invention, provided for illustration purposes with reference to the appended figures, in which:

FIG. 1 shows a system for certifying a detection of a gaseous substance according to one example embodiment, FIG. 2 shows an ignition interlock mechanism integrating a system for certifying a detection according to one example embodiment, FIG. 3 shows one example of a flow chart of the main steps of a method for preventing the start-up of a vehicle, FIG. 4 shows one application in the field of transport using a detection certification system, FIG. 5 shows the main components of a remote server allowing the detection status of members of an organisation to be managed, FIG. 6 shows one example of a flow chart of the main steps of a method for managing the detection status of members of an organisation.

6. DESCRIPTION OF ONE EMBODIMENT OF THE INVENTION 6.1 General Principle

The invention concerns a system for certifying a detection of a gaseous substance present in the air exhaled by an individual. The system comprises a sensor detecting said gaseous substance in the exhaled air, said sensor comprising a unit for collecting and analysing a sample of air exhaled by said individual, capable of providing a measurement of the quantity of gaseous substance per unit of volume. The system further comprises a portable terminal equipped with a means for communicating with the sensor so as to at least receive the measurement. The portable terminal is equipped with a camera intended to capture an image of the individual blowing into said sensor to perform a detection, and a module for authenticating the individual and the sensor used for said exhaled air sample by analysing the data of images using facial recognition for the individual and by analysing a graphic marker placed on the sensor. The terminal produces a set of information comprising an item of data representative of the quantity of gaseous substance measured in the sample and a piece of authenticated identification data of said individual who has exhaled said sample. In this way, the system can at the same time authenticate the identity of the person who carries out the test, authenticate the sensor used for the test, and associate the result of the value of the detection with said person.

6.2 Specific Embodiment

FIG. 1 shows a system for certifying a detection of a gaseous substance according to one example embodiment. The system 1 shown comprises a portable terminal 2 equipped with a means for communicating with a network, such as a mobile phone network and a user interface 3 such as a screen and a keypad. This interface can alternatively comprise a touch-sensitive screen or a voice-recognition unit designed to receive commands and transmit information to a user. The terminal 2 comprises a software module for downloading applications originating from the telephony network and a module for running the applications downloaded. The terminal 2 is also equipped with a camera 4 capable of capturing photographs or videos, in particular of the user thereof, who can hold it at arm's length. Said user can be the driver or any other person, such as an adult accompanying a minor during supervised driving. The system further comprises a sensor 5 comprising a unit for collecting and analysing a sample of air exhaled by said individual, capable of providing a measurement of the quantity of gaseous substance per unit of volume. Said gaseous substance is preferably a psychotropic substance and in particular includes alcohol, *cannabis* and heroin. The sensor 5 can be provided with a display means 6. The sensor 5 comprises a mouthpiece 7 allowing the user thereof to exhale a breath containing or not containing said gaseous substance into a duct 8 where it is analysed, whereby the exhaled air escapes from an end of the duct 8 that is opposite to the mouthpiece 7. The sensor 5 is in communication with the portable terminal 2 by a wired or wireless computer link 9 (such as WiFi).

By connecting to a remote site, the terminal 2 downloads the APLY application allowing a detection to be authenticated. Once downloaded, the APLY application activates the camera 4 and the sensor 5 and informs the user that the test is ready to be carried out. According to an improvement, the terminal 2 initialises communication with the sensor 5 in order to ensure that a single sensor is connected. The user directs the camera lens towards himself/herself such that a part of his/her face appears in the images captured. Ideally, at least one image is captured when the user blows into the mouthpiece 7, however this is not compulsory, whereby the images can be captured shortly before or after the test. The sensor currently used requires a warm-up time, which can be used to take a photograph and identify the person. At least part of the face of the user and the sensor 5 are visible in the image captured. According to the invention, the sensor 5 used has a graphic marker 10 allowing it to be identified among all other sensors. Said marker is, for example, a barcode or a QR-code, or any graphical symbol appearing on the side of the sensor opposite that of the mouthpiece. Said marker can also be a light element, such as a LED or an indicator, one luminous feature of which at least identifies the sensor. For example, the diode is controlled by a PWM generator, the frequency and duty cycle of which are specific to said sensor, and cannot be attributed to another sensor. Said light signals are captured and analysed by the camera of the terminal. The frequency and duty cycle are also transmitted by the link 9 for comparison. Advantageously, the features of the light beam identifying said sensor are provided by the portable terminal 2. In this way, only the sensor in communication with the terminal can know said features, thus ensuring that a single sensor is connected to said terminal.

The APLY application analyses the data of the one or more images captured in order to search for a face, then to identify the user through facial recognition. The APLY application also searches for the presence of the graphic marker 10, and if detected, analyses same to extract the identifier thereof. The analysis of the image can take place during a sensor warm-up step and/or at the time of the measurement. In all cases, the capture of images and the measurement of the sensor take place at times that are very close to one another to ensure that the person photographed is the person blowing into the breathalyser. Advantageously, the screen of the terminal 2 displays indications assisting the user in carrying out the test. These indications are, for example:

"Position your face in the centre",
"Bring the sensor's mouthpiece to your mouth",
"Keep your face in the centre of the image and stay still",
"Hold the sensor from the bottom",
"Take a deep breath then blow".
"Thank you! The test is complete".

The terminal warns the user when the sensor is operational by means of a light signal (message displayed on the screen 6, lighting of the LED, light flash, etc.) or audible signal, or by a vibration. The appearance of said light and/or audible signal triggers the capture of at least one image with the camera 4, during this time the sensor 5 analyses the breath exhaled by the user and passing through the duct 8 to determine the level of psychotropic substances. If the image captured does not allow the user and the sensor to be identified, a message appears on the screen 3 requesting that the user repeats the test. The main reasons for failure of a test are:
- the user was not recognised,
- the sensor was not recognised,
- the face left the field of the camera,
- other faces were present in the image,
- the process duration was too long,
- the quality of the image captures is insufficient (lighting, contrast, focus)
- the quality of the reference image is insufficient.

The APLY application receives the item of data representative of the measurement of the quantity of gaseous substance per unit of volume, and the identifier of the sensor, from the sensor 5 via the link 9. The application can then compare the identifier received with that extracted from the image of the sensor and compare the two. If the identifiers match, the sensor is authenticated; conversely, an error message is displayed. The application identifies the user by facial recognition and once said checks have been performed, said application associates the measurement with the identity of the user having carried out the test. In this way, any cheating involving the user carrying out the test is practically impossible to achieve.

Such a system can be used in many applications. This invention provides for the integration of said system into an ignition interlock mechanism of a vehicle, and into a method for checking the status of the members of an organisation.

6.3 Application in an Ignition Interlock Mechanism

FIG. 2 shows an ignition interlock mechanism integrating a system for certifying a detection. Said mechanism is present in a vehicle 11 that comprises an on-board computer 12 communicating in particular with the electronic ignition of the engine, with the fuse box of the vehicle, or with a signal jamming device preventing the signal emitted by a contactless key from travelling. According to an alternative embodiment, the mechanism controls the vehicle's horn and triggers an effect similar to that of a theft when the detection is positive. Through this communication, the on-board computer 12 can prevent engine start-up when the driver 13 uses his/her ignition key and when certain conditions concerning the state of health of the driver are not respected, said state being provided by the aforementioned detection certification system 1. The on-board computer is provided with a module for communicating with the portable terminal 2 of the driver, said communication preferably taking place by short-range radio link (for example using "Bluetooth"), however can also take place by a wired connection (for example via a "USB" port).

One embodiment of a method for preventing the start-up of a vehicle is explained by the flow chart in FIG. 3, which is provided for illustration purposes. This flow chart shows the steps of an application using the system 1.

In step 3.1, the driver enters the vehicle and requests start-up using the ignition key. The computer receives the start-up command in the form of a signal and informs the driver of the need to carry out a psychotropic substance detection test (step 3.2). This information can be transmitted by display on a screen or by a digital voice announcement. The on-board computer then asks the driver to launch the APLY application on his/her terminal. In step 3.3, the on-board computer initiates communication with the portable terminal 2 and waits for the data produced by the test. The portable terminal activates the sensor 5 and informs the driver when the sensor is operational (step 3.4). To prepare the driver for the test, the terminal informs him/her using its screen 3 of the conditions for carrying out the test. These conditions consist of the camera of the driver being placed facing the latter, potentially by securing to the rear-view mirror as shown in FIG. 3, so that the data of the image captured at this time contains both the face of the driver and the side of the sensor on which the graphic marker is located.

In step 3.5, the terminal receives the measurement data originating from the sensor and analyses the one or more images captured by the camera. The APLY application runs a facial recognition task in order to determine the identity of the person present in the photo. This technology is known per se and is used to provide an identity with a maximum accuracy level. The APLY application also runs a program to search for the graphic marker present on the sensor and to decode said graphic marker in order to extract the identifier associated with the sensor. The sensor 5 further transmits the result of the measurement and its identifier via the link 9 thereof to the terminal 2. The terminal then compares the identifier received from the sensor with the decoded identifier of the graphic marker (step 3.6). If the identifiers are not identical, the driver could be suspected of cheating and the terminal 2 transmits a signal to the on-board computer 12 showing the measurement to have failed. After receiving said signal, the computer will not authorise engine start-up (step 3.7). If, however, the identities match, the breath analysed is therefore that of the person present in front of the camera 4 and holding the sensor 5. In such a case, in step 3.8, the APLY application compares the data item representative of the quantity of gaseous substance per unit of volume with a threshold value. The threshold concerning the blood alcohol level is, for example, 0.5 grams per litre of blood. If the threshold is exceeded, the terminal 2 transmits a signal to the on-board computer 12 indicating that the identity of the driver has been verified, but that he/she is not in a condition to drive. A message such as "replace driver" can be shown (step 3.9). If, however, the blood alcohol threshold is not exceeded, and if no drugs are detected, the computer authorises engine start-up (step 3.10).

The application thus described is used to ensure that the driver has carried out the test with a high safety level. According to a known technique, the sensor 5 is provided with a micro-anemometer 14 integrated into the duct 8, which in particular checks the flow of exhaled air and checks that the volume thereof is sufficient; more specifically, only alveolar air contains alcohol and the user must continuously blow a certain volume of air in order to exhale said alveolar air. According to one optional improvement, as soon as the micro-anemometer detects the presence of a breath, the sensor transmits a signal to the terminal 2 indicating the start of the measurement, which triggers the capture of at least one first image. If the micro-anemometer detects the end of the breath, the measurement is complete and the measurement value of the level of psychotropic substances is transmitted to the terminal.

6.4 Application in a Mechanism for Checking the Detection Status of the Members of an Organisation The system for certifying a detection of a gaseous substance can also be used to check the detection status of members of an organisation, said detection producing a high safety level. The term "organisation" describes any group of individuals responsible for performing a certain job requiring a good state of health and under the responsibility of an authority. An organisation is, for example, a transport operator whereby drivers transport passengers travelling journeys. This can also be workers in a factory, window cleaners, builders, etc. and in general any profession for which an employee must be in full possession of his/her faculties.

FIG. 4 shows such an application in the field of transport, for example buses 20 carrying passengers. During his/her journey, the bus 20 crosses geographic areas covered by telephone networks represented by base stations 21, belonging to a mobile phone operator such as a 3G/4G operator. The bus driver is equipped with the aforementioned system 1. The portable terminal 2 initiates communication with the different base stations 21 and is provided with a position determination means. This means can be the telephone network itself, analysing, by triangulation, the return times of communications with a plurality of base stations. This means can also be a GPS (Global Positioning System) module integrated into the terminal. In any case, the determination of the position of the terminal, and thus that of the bus driver, is transmitted via the telephone network to a so-called "organisation member management" (or OMM) remote server 22.

FIG. 5 shows the main components of an OMM server 22. According to this example embodiment, the OMM server 22 comprises an ALU central processing unit 23 connected to a PM executable program memory 24, and a HD hard disk 25 containing a database for storing data in a non-volatile manner. The program memory comprises an OMM application for managing the members of the organisation and for obtaining at least the most recent detections carried out therewith. The server 22 further contains an I/O interface 26 for communication with the telephone network. The messages received by the I/O interface allow the receipt of data on the detections carried out with the different drivers travelling journeys. The connection means may differ depending on the type of device in communication; therefore, the optimisation server 23 can communicate with the telephones via a wireless network (3G/4G mobile telephony) or by a cable via any digital network (for example the Internet).

After having described the main component elements of said application, the manner in which they engage with one another shall now be described.

One embodiment of an application for managing the state of health of members is explained by the flow chart in FIG. 6, which shows one preferred example embodiment. The example flow chart shows the steps of one example of the implementation of the method according to the invention.

In a prior step 6.1, the server 23 initialises, in the memory 25 thereof, a table containing rows corresponding to each member of the organisation. Each row of the table contains the following information:
The identity (first name and last name) of the member and their telephone number,
biometric data identifying the member's face,
the date and time of the last test,
the state of the last test.

At a given time, a staff need appears and a step of searching for at least one member capable of performing a given job is launched. The OMM application then calls up a list of members and asks them to carry out the detection test (step 6.2). The test is carried out using the system described in paragraph 6.2. As soon as the first results are received by the server, they are recorded in the memory 25 (step 6.3). Advantageously, the location of the detection place is also recorded. In step 6.4, at least one member is selected for the job to be performed. Of course, said selected members must have received a negative detection result. The members selected are then contacted to provide them with the instructions to be followed in order to perform the job requested.

According to an improvement, during the performance of the job, the member is contacted by his/her portable terminal 2 to perform a repeat detection (step 6.5). The triggering of said repeat detections can occur at regular time intervals, for example every 3 hours. Alternatively, triggering occurs at random times, for example within a time interval of one to 6 hours after the last test.

If a repeat test cannot be carried out, doubts are raised concerning the detection status of said member. In such a case, the server can trigger an alarm for the replacement of said member by another member, said other member having previously received a negative detection result.

According to an improvement, if the detection result is positive, a message is transmitted to at least one third party, the identity of whom is recorded in the server 23. The message can be transmitted by any means: SMS, e-mail, telephone voice call, etc. This person can be a parent (within the scope of family monitoring for example) or a line manager or safety agent (within the scope of use at the workplace and remote detection), or a medical advisor or healthcare professional.

According to an improvement that applies primarily to an organisation in the field of transport, the OMM server monitors the movement of the members in real time and determines whether said members are moving or stationary. A repeat detection is triggered if the member is not moving within his/her vehicle, or in other words if his/her travel speed is less than 5 kilometres per hour for example. Above this value, it can be considered that the driver is behind the wheel and that it is not the right time to distract him/her. According to another improvement, the test can be carried out when the OMM server detects immobilisation for at least a given period of time, then a movement at less than a given speed (typically 5 km/h, which can mean that the driver is returning to his/her vehicle on foot after taking a break). It could be assumed that the driver has taken a lunch break and that it should now be checked whether he/she has consumed alcohol.

According to an alternative embodiment, the terminal 2 received signals by short-range radio, said signals originating from local transmitters and triggering the detection (step 6.6). This alternative embodiment occurs, for example, upon activation of the ignition key of a vehicle, or upon the start-up of the machine on which the worker is working. This alternative embodiment can also be used if surveillance cameras detect the unusual behaviour of an employee. According to this alternative embodiment, once the test has been carried out, the terminal 2 transmits the results to the OMM server for recording in the memory 25. This alternative embodiment can be perfectly combined with the fact that the server also requests the performance of tests. In such a case, the OMM server records the equipment having triggered the test in the memory 25, said equipment being either a local equipment item or the server.

6.5 Application for Managing Medical Files

The system for certifying a detection of a gaseous substance can also be used to update remote medical data. The patients are invited to perform detections at certain times and the values thus measured are transmitted by the telephone network and recorded in a remote server. Depending on the patients, detection requests are emitted at random times during a given period of time, or at fixed times, or during said patient's "craving" periods (i.e. at times when he/she has an uncontrollable urge to drink). The server can be viewed by healthcare professionals who can obtain the level of psychotropic substances exhaled by a patient, and thus review his/her progress over time. This progress is particularly useful during withdrawal, in particular to help a person no longer be dependent on alcohol. Access to data on the server is secured such that only the healthcare professionals and/or the patient can view the data recorded. Authorising the patient to access the data is helpful as it allows him/her to see that the efforts made are producing results. Depending on the value of the level detected, messages are sent to the people: congratulating messages if the values are low, messages of encouragement, or messages asking the person to contact a healthcare professional.

The invention is not limited to the aforementioned embodiments. In particular, the system can be used for all human activities where the measurement of the level of psychotropic substances associated with an individual must be checked to be below a given threshold.

The invention claimed is:

1. A system for certifying a detection of a gaseous substance present in the air exhaled by an individual, said system comprising:
   a sensor detecting said gaseous substance in the exhaled air, said sensor comprising a unit that collects and analyzes a sample of air exhaled by said individual, capable of providing a measurement of the quantity of gaseous substance per unit of volume;
   a portable terminal equipped with a communication device for communicating with the sensor so as to at least transmit the measurement, wherein the portable terminal is equipped with a camera to capture an image of the individual blowing into this sensor to perform a detection, and with an authentication module to authenticate the individual and the sensor used for said exhaled air sample by analysing data of the image using facial recognition for the individual and by analysing a graphic marker placed on this sensor, the terminal producing a set of information comprising an item of data representative of the quantity of gaseous substance measured in the sample and authenticated identification data of the individual who has exhaled said sample; and
   a remote device communicating by radio with the portable terminal, the remote device configured to emit a signal to the portable terminal, this signal triggering appearance of a menu displayed on a screen of the portable terminal and requesting completion of a test, the portable terminal configured to emit an information item to said remote device via radio, this information item being representative of the measurement and the authenticated identification data of the individual,
   wherein the portable terminal has a position determination means allowing the remote device to obtain a position thereof, the remote device emitting the signal to the portable terminal to trigger the appearance of the menu after an immobilisation of the terminal for a minimum period of time.

2. The system according to claim 1, further comprising a control device in communication with the terminal, said control device controlling operation of a vehicle and authorising start-up thereof if the individual identified by the data received is authorised to drive said vehicle and if the transmitted measurement shows that the gaseous substance is not present or the quantity of the gaseous substance is present below a certain threshold.

3. The system according to claim 1, further comprising means for emitting a sound integrated into a vehicle, the means for emitting a sound being activated when the transmitted measurement shows that the quantity of the gaseous substance is present beyond a certain threshold.

4. The system according to claim 1, wherein the remote device triggers an alarm if no test producing a negative result has been correctly carried out during a given period of time.

5. The system according to claim 1, wherein the portable terminal detects activation by the individual of a device for use thereof, the activation triggering the appearance of the menu requesting said individual to carry out a test.

6. The system according to claim 1, wherein said sensor comprises an anemometer detecting an airflow resulting from an exhalation, the detection of an airflow resulting from an exhalation triggering the capture of at least one image.

7. The system according to claim 1, wherein the graphic marker of the sensor is a visible indicator light on a side opposite that of a mouthpiece into which the individual blows when carrying out a test, a light beam emitted by said indicator having features that identify said sensor.

8. The system according to claim 7, wherein at least one feature of the light beam emitted by the visible indicator light on the side opposite that of the mouthpiece is provided by the portable terminal via the communication device.

9. The system according to claim 1, wherein the graphic marker is a QR Code or a barcode placed on a side opposite that of a mouthpiece of the sensor.

10. The system according to claim 1, wherein the terminal is configured to initialize communication with the sensor and to limit a number of sensors connected to the portable terminal to one.

11. The system according to claim 1, wherein said remote device is configured to progressively record the measurements taken over time, and provides secure access to said measurements for a healthcare professional and/or for the user.

12. The system according to claim 1, wherein said remote device is provided with means for alerting a healthcare professional or any other authority in an event that no detection is carried out or if positive detection results are obtained by a user dependent thereon.

13. A method for certifying a detection of a gaseous substance present in air exhaled by an individual using a sensor detecting said gaseous substance in the exhaled air, wherein said method comprises:
   exhaling by said individual into the sensor in order to provide a measurement of the quantity of gaseous substance per unit of volume,
   capturing an image of at least the individual exhaling into said sensor in order to carry out a test, using a camera of a portable terminal connected to said sensor,
   authenticating, by the terminal, the individual and the sensor used for said exhaled air sample by analysing data of the image using facial recognition for the individual and by analysing a graphic marker placed on the sensor,
   producing, by the terminal, a set of information comprising an item of data representative of the quantity of gaseous substance measured in the sample and authenticated identification data of the individual who has exhaled said sample, and
   communicating, by the terminal, with a remote device by radio, the communicating comprising:
      the portable terminal receiving a signal emitted by the remote device based on a position of the portable terminal, this signal triggering appearance of a menu displayed on a screen of the portable terminal and requesting completion of a test after an immobilisation of the portable terminal for a minimum period of time, and the portable terminal emitting an information item to said remote device which is representative of the measurement and the authenticated identification data of the individual.

14. A system for certifying a detection of a gaseous substance present in the air exhaled by an individual, said system comprising:

a sensor detecting said gaseous substance in the exhaled air, said sensor comprising a unit that collects and analyzes a sample of air exhaled by said individual, capable of providing a measurement of the quantity of gaseous substance per unit of volume; and a portable terminal equipped with a communication device for communicating with the sensor so as to at least transmit the measurement, wherein the portable terminal is equipped with a camera to capture an image of the individual blowing into this sensor to perform a detection, and with an authentication module to authenticate the individual and the sensor used for said exhaled air sample by analysing data of the image using facial recognition for the individual and by analysing a graphic marker placed on this sensor, the terminal producing a set of information comprising an item of data representative of the quantity of gaseous substance measured in the sample and authenticated identification data of the individual who has exhaled said sample, wherein the portable terminal is configured to initialize communication with the sensor and to limit a number of sensors connected to the portable terminal to one.

15. The system according to claim 14, wherein said remote device is configured to progressively record the measurements taken over time, and provides secure access to said measurements for a healthcare professional and/or for the user.

16. A method for certifying a detection of a gaseous substance present in air exhaled by an individual using a sensor detecting said gaseous substance in the exhaled air, wherein said method comprises:

the portable terminal initializing communication with the sensor and limiting a number of sensors connected to the portable terminal to one, the sensor collecting and analysing a sample of air exhaled by said individual into the sensor in order to provide a measurement of the quantity of gaseous substance per unit of volume, receiving, by the portable terminal the measurement from the sensor, capturing an image of at least the individual exhaling into said sensor in order to carry out a test, using a camera of a portable terminal connected to said sensor, authenticating, by the portable terminal, the individual and the sensor used for said exhaled air sample by analysing data of the image using facial recognition for the individual and by analysing a graphic marker placed on the sensor, and producing, by the terminal, a set of information comprising an item of data representative of the quantity of gaseous substance measured in the sample and authenticated identification data of the individual who has exhaled said sample.

17. The method according to claim 16, further comprising:

the portable terminal communicating by radio with a remote device to emit an information item to the remote device which is representative of the measurement and the authenticated identification data of the individual, and the remote device progressively recording the measurements taken over time, and providing secure access to said measurements for a healthcare professional and/or for the user.

* * * * *